United States Patent [19]

Chaberek

[11] 3,984,453

[45] Oct. 5, 1976

[54] PROCESS FOR PREPARING NITRILOTRIACETONITRILE

[75] Inventor: Stanley Chaberek, Skaneateles, N.Y.

[73] Assignee: Stauffer Chemical Company, Westport, Conn.

[22] Filed: Nov. 3, 1971

[21] Appl. No.: 198,015

Related U.S. Application Data

[63] Continuation of Ser. No. 630,875, April 14, 1967, abandoned, which is a continuation-in-part of Ser. No. 545,435, April 26, 1966, abandoned.

[52] U.S. Cl. .................................... 260/465.5 A
[51] Int. Cl.[2] ................ C07C 120/00; C07C 121/43
[58] Field of Search ................... 260/465.5, 465.5 A

[56] References Cited

UNITED STATES PATENTS

| | | | |
|---|---|---|---|
| 2,855,428 | 10/1958 | Singer et al. | 260/465.5 A |
| 3,061,628 | 10/1962 | Singer et al. | 260/465.5 A |
| 3,679,728 | 7/1972 | Morgan et al. | 260/465.5 A |
| 3,679,729 | 7/1972 | Daniels | 260/465.5 A |

FOREIGN PATENTS OR APPLICATIONS

| | | | |
|---|---|---|---|
| 1,159,959 | 12/1963 | Germany | 260/465.5 |
| 974,787 | 11/1964 | United Kingdom | 260/465.5 |

*Primary Examiner*—Joseph Paul Brust
*Attorney, Agent, or Firm*—Daniel S. Ortiz

[57] ABSTRACT

The preparation of methylene-bis-iminodiacetonitrile and nitrilotriacetonitrile by the reaction of formaldehyde, ammonia and hydrogen cyanide under acidic conditions involving a particular procedure of adding hydrogen cyanide to an acidified liquid phase adduct of ammonia and formaldehyde; the preparation of nitrilotriacetonitrile from methylene-bis-iminodiacetonitrile; and the preparation of nitrilotriacetic acid from methylene-bis-iminodiacetonitrile by carboxymethylation under alkaline conditions. Nitrilotriacetonitrile is particularly useful in the formation, by hydrolysis, of nitrilotriacetic acid of particular value as a chelating or complexing agent.

32 Claims, 1 Drawing Figure

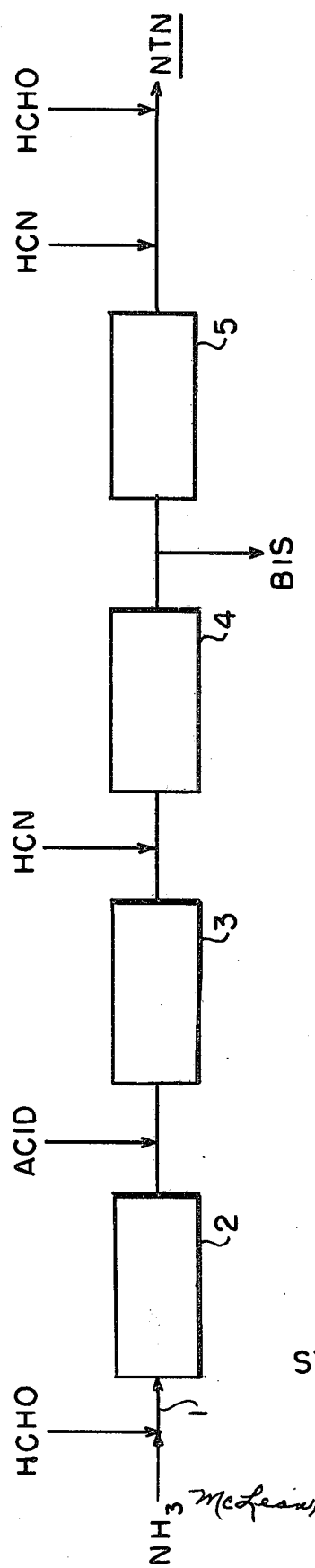

PROCESS FOR PREPARING NITRILOTRIACETONITRILE

CROSS REFERENCE TO RELATED APPLICATIONS

This application is a continuation of application Ser. No. 630,875, filed Apr. 14, 1967, now abandoned, which in turn is a continuation-in-part of application Ser. No. 545,435, filed Apr. 26, 1966, now abandoned.

BACKGROUND OF THE INVENTION

1. Field of the Invention

My invention relates to the preparation of nitrilotriacetonitrile, which is particularly useful in the formation, by hydrolysis, of nitrilotriacetic acid of particular value as a chelating or complexing agent. More particularly, my invention relates to the preparation of methylene-bis-iminodiacetonitrile and to the preparation of nitrilotriacetonitrile from the methylene-bis-iminodiacetonitrile and also to the preparation of nitrilotriacetic acid directly from the methylene-bis-iminodiacetonitrile.

2. Description of the Prior Art

In alkaline processes for the preparation of nitrilotriacetic acid salts, the formation of the intermediate nitrile and its hydrolysis to the nitrilotriacetic acid salt occur simultaneously. Alkaline processes include the classical carboxylation of ammonia with sodium cyanide and formaldehyde and processes in which partially carboxymethylated derivates such as glycine and iminodiacetic acid are used. Thus the carboxymethylation of glycine with sodium cyanide and formaldehyde or with glycolonitrile has been described. These processes, however, are intrinsically inferior to acid processes because side reactions involving formaldehyde and ammonia lead to the formation of substantial quantities of inert materials.

In acid processes, the nitrilotriacetonitrile produced may be isolated and then hydrolyzed to the nitrilotriacetic acid. Such processes include the preparation of the nitrile by the reaction of aminoacetonitrile with formaldehyde and an excess of hydrogen cyanide, as described in U.S. Pat. No. 2,405,966 to Loder; the addition of sodium cyanide to a hydrochloric acid solution of an ammonium salt and formaldehyde, as described in U.S. Pat. No. 2,205,995 to Ulrich and Ploetz; the addition of ammonia to a mixture of acid-stabilized formaldehyde and liquid hydrogen cyanide, as described in U.S. Pat. No. 2,855,428 to Singer and Weisberg; and the addition of hexamethylenetetramine to an acid-stabilized mixture of liquid hydrogen cyanide and formaldehyde, as described in U.S. Pat. No. 3,061,628 to Singer and Weisberg.

The acid processes, however, are characterized either by low yields and recycle problems caused by byproducts, e.g. inorganic salts, as in Loder and in Ulrich and Ploetz or by hazardous and inherently limited operating conditions as in the Singer and Weisberg processes. In these latter processes, a mass of hydrogen cyanide in excess is used in a closed reaction zone, i.e. a container or reaction pot, presenting the hazards of confining a highly toxic, flammable substance in a potentially explosive reaction. Moreover, the fixed volume of the container inherently limits rates of addition of reactants.

SUMMARY OF THE INVENTION

I have now devised a novel method of reacting ammonia, formaldehyde and hydrogen cyanide which provides a process providing excellent yields of essentially pure nitrilotriacetonitrile while providing the particular advantages of ease and safety of operation in handling cyanide in large amounts and adaptability to recycling. I have found that the addition of hydrogen cyanide to a liquid phase adduct of ammonia and formaldehyde maintained under strong acid conditions produces methylene-bis-iminodiacetonitrile in excellent yields and that this compound can be reacted with formaldehyde and liquid hydrogen cyanide to produce nitrilotriacetonitrile in excellent yields and purity. I have also found that methylene-bis-iminodiacetonitrile, although a tertiary amine, can be carboxymethylated under alkaline conditions to nitrilotriacetic acid.

My invention provides a process in which only small amounts of hydrogen cyanide are present at any one time thus providing improved safety and ease of handling of this hazardous substance. The process is adaptable to practice in small equipment and a continuous reaction zone such as a pipe thus avoiding the inherent limitations of a reaction pot or container. Moreover, the process is advantageously adaptable to recycling because of the absence of byproducts.

DETAILED DESCRIPTION OF THE INVENTION

In the preparation of methylene-bis-iminodiacetonitrile, the liquid phase adduct of ammonia and formaldehyde is preferably formed by adding ammonia to formaldehyde maintained at a relatively low temperature. Anhydrous ammonia is preferred to aqueous solutions as higher yields are obtained. The rate of addition of ammonia is controlled to keep the temperature low. The temperature is maintained below about 50° C. and preferably between about 10° C. and about 35° C. for the best yields. The pH of the liquid phase is then adjusted to a strong acid level, i.e. between about 2 and 0 and preferably about 1 or less for the best yields. The pH is controlled by the addition of acids such as sulfuric acid or hydrochloric acid. Liquid hydrogen cyanide is then added to the liquid phase adduct while maintaining the temperature below about 50° C. and preferably below about 35° C. The ammonia, formaldehyde and hydrogen cyanide are used in the amounts stoichiometrically necessary for the formation of the methylene-bis-iminodiacetonitrile, i.e. in a molar ratio of two moles of ammonia, five moles of formaldehyde and four moles of hydrogen cyanide to provide one mole of methylene-bis-iminodiacetonitrile. A small excess of hydrogen cyanide can be used to offset any losses of hydrogen cyanide. In order to avoid formation of byproducts, it is important to add the hydrogen cyanide at a rate which balances the rate of decomposition of the ammonia-formaldehyde adduct. The methylene-bis-iminodiacetonitrile forms in essentially quantitative yields and can be recovered as a solid from the liquid phase, for example, by cooling and filtering.

To form nitrilotriacetonitrile, methylene-bis-iminodiacetonitrile is reacted with liquid hydrogen cyanide and formaldehyde. The reaction can be carried out by adding formaldehyde to a liquid phase mixture of methylene-bis-iminodiacetonitrile and liquid hydrogen cyanide or by adding liquid hydrogen cyanide to a liquid phase mixture of methylene-bis-iminodiacetonitrile and formaldehyde. In the method where formaldehyde is added to the mixture of methylene-bis-iminodiacetonitrile and hydrogen cyanide, some formaldehyde can be added initially to the mixture and then the remainder added. The temperature is preferably maintained between about 50° and about 85° C. although temperatures as high as about 95° C. can be used but a less pure product is obtained. A temperature of about 65° to about 70° C. gives the best product. Stoichiometric amounts of the reactants are used, i.e. in a molar ratio one mole of methylene-bis-iminodiacetonitrile, one mole of formaldehyde and two moles of hydrogen cyanide to provide two moles of nitrilotriacetonitrile. A small excess of hydrogen cyanide can be used to offset losses of this material. The nitrilotriacetonitrile forms in essentially quantitative yields and can be recovered as a solid of high purity from the liquid phase, for example by cooling and filtering. The nitrilotriacetonitrile can be readily converted into nitrilotriacetic acid by hydrolysis by well-known methods.

The two steps described above can also be advantageously performed without the isolation of the intermediate methylene-bis-iminodiacetonitrile. In this modification, the methylene-bis-iminodiacetonitrile is formed by the addition of liquid hydrogen cyanide to the liquid phase ammonia-formaldehyde adduct maintained under the conditions described above and then liquid hydrogen cyanide and formaldehyde are added to the liquid phase containing the methylene-bis-iminodiacetonitrile to form nitrilotriacetonitrile. The stoichiometric amount of formaldehyde required for the reaction with methylene-bis-iminodiacetonitrile to form the nitrilotriacetonitrile can be added either entirely in this step or an excess of formaldehyde can be used in the formation of the ammonia-formaldehyde adduct in the first step so that in the second step only that remaining amount of formaldehyde required need be added, i.e. part or all of the formaldehyde needed for the reaction of the second step can be added in the first step. Similarly, part or all of the hydrogen cyanide needed for the reaction of the second step can be added in the first step. The overall stoichiometric quantities required for the formation of two moles of nitrilotriacetonitrile are six moles of hydrogen cyanide, two moles of ammonia and six moles of formaldehyde. The reaction can also be carried out in a cyclic manner by recovering the filtrate from the completed reaction and utilizing it in a subsequent reaction.

The process can advantageously be carried out in a continuous manner in a tubular reaction zone, such as a pipe as illustrated in the accompanying schematic drawing. As shown in the drawing, ammonia and formaldehyde, to form the adduct, are introduced into a tube 1 and flow through a temperature control zone 2 to maintain the desired temperature as described above. At this point, the pH is about 8 to 10 and acid is introduced to the tube to lower the pH to a strong acid value, e.g. 1 or below, and this mixture flows through another temperature control zone 3 to maintain the desired temperature, following which hydrogen cyanide is added and methylene-bis-iminodiacetonitrile (BIS) is formed. The methylene-bis-iminodiacetonitrile can be recovered by cooling and filtering as illustrated by 4 or passed without isolation through a temperature control zone 5 to achieve the desired temperature, following which liquid hydrogen cyanide and formaldehyde are added and nitrilotriacetonitrile (NTN) is formed and recovered. It will be understood, of course, that the illustrated system can be modified as to the manner, amount and point of addition of the formaldehyde and hydrogen cyanide as described above and in the examples below.

In another advantageous modification, a mixture of ammonia and hydrogen cyanide is added to the ammonia-formaldehyde adduct. This is particularly advantageous due to the commercial availability of gas mixtures consisting essentially of ammonia and hydrogen cyanide, e.g. the mixture recovered from the process of preparing hydrogen cyanide from methane, oxygen and ammonia. Ammonia and hydrogen cyanide can be added to the fully formed or the partially formed ammonia-formaldehyde adduct. By fully formed adducts, I mean adducts with sufficient stoichiometric quantities of ammonia and formaldehyde to form nitrilotriacetonitrile, i.e. in a molar ratio of 1:3. By partially formed adducts, I mean those adducts where there is an insufficient stoichiometric quantity of ammonia present. When a mixture of ammonia and hydrogen cyanide is added to the fully formed adduct, much of the ammonia is not used and should subsequently be recovered. But when the mixture is added to the partially formed adduct, depending upon the stoichiometric relationships, most of the ammonia is utilized. When a mixture of ammonia and hydrogen cyanide is added to the ammonia-formaldehyde adduct, the molar ratio of ammonia to formaldehyde to the adduct preferably lies between about 1:2.5 to about 1:9. The ammonia to hydrogen cyanide molar ratio in the mixture can be varied, but preferably lies between about 1:4.5 and about 1:18. The mixture can be added over a range of temperatures. The preferred temperature range is about 30° C. to about 70° C. In fact, the mixture can be preferably added in two stages, each at a different temperature, for example, first at 30° C. and then at 65° C. The amount of the mixture added in each stage can vary widely. Another type of two-stage addition scheme can be used and is preferred when used in conjunction with the two temperature level scheme. Pure hydrogen cyanide can be used in place of the NH$_3$—HCN mixture as the additive in the second stage. This preferred mode is illustrated in Example 22, wherein the best experimental results were obtained. Example 22 utilized a partially formed adduct, and used hydrogen cyanide, plus formaldehyde, in the second stage. Also, the formaldehyde may be added all at once in the adduct forming step, or part of it can be added in one of the NH$_3$—HCN or HCN addition stages. The sequence of adding the various reactants and mixtures thereof is illustrated in the various examples below, wherein the preferred molar ratios and optimum reaction conditions are reflected in terms of such factors as yields, conversion percentages, etc. In some of the examples, nitrilotriacetonitrile is formed, but in others, due to the reacton conditions, the molar ratios of reactants, etc., methylene-bis-iminodiacetonitrile or combinations of both are formed.

The mixture of ammonia and hydrogen cyanide that is added to the adduct of ammonia and formaldehyde is understood to encompass the simultaneous addition of the ammonia and hydrogen cyanide, or the pre-mixing of those reagents in a mixer before such addition, or any similar and suitable scheme.

The methylene-bis-iminodiacetonitrile can also be directly converted to a nitrilotriacetic acid salt by carboxymethylation under alkaline conditions. In carrying out this process, methylene-bis-iminodiacetonitrile, as a solid or in aqueous solution, is added to a solution of sodium hydroxide and sodium cyanide wherein the cyanide is in molar excess over the nitrile during the reaction following which formaldehyde is added in proper stoichiometric amount and the sodium salt of nitrilotriacetic acid is formed. The presence of excess cyanide in the first stage of the reaction prevents the loss of methylene-bis-iminodiacetonitrile in side reactions, and utilizes the mole of formaldehyde released from the nitrile following which the remaining necessary amount of formaldehyde is added. Thus, by careful control of formaldehyde addition optimum yields are obtained.

While sodium cyanide is preferred, other alkali metal cyanides such as potassium cyanide can be used. Also, the alkali metal cyanide can be added as such or generated in situ in the alkaline solution by use of an excess of the alkali metal hydroxide and the addition of Hydrogen Cyanide. Except for the use of an excess of cyanide, the reactants are used in stoichiometric proportions, i.e. in a molar ratio of one mole of methylene-bis-iminodiacetonitrile, four moles of sodium hydroxide, one mole of formaldehyde and two moles of sodium cyanide stoichiometrically required to provide two moles of the sodium salt of nitriloacetic acid. The reaction is carried out preferably at elevated temperature to insure complete removal of all ammonia generated. Temperatures in the range of about 70° C. to 110° C. can be used. Small excesses of formaldehyde and sodium cyanide over stoichiometric amounts can be used to offset their losses in side reactions.

My invention will be further illustrated by the following examples.

EXAMPLE 1

Preparation of Methylene-bis-Iminodiacetonitrile,

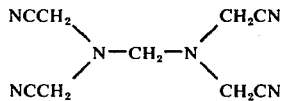

Formaldehyde (31.5 ml; 0.42 moles; 40g/100 ml) was charged into a water-jacketed flask and cooled to 10 to 15° C. Anhydrous ammonia gas (4.76 g; 0.28 mole) was passed into the flask, the rate of addition was adjusted in such a way that the temperature of the reaction did not rise above 25° C. After the addition of ammonia, the ammonia-formaldehyde adduct was stirred for an hour, formaldehyde (21.5 ml; 0.28 mole) was added and the pH was adjusted to one, by addition of concentrated sulfuric acid. Then liquid hydrocyanic acid (15.12 g; 0.56 mole) was added at the rate of 0.44 ml/min. while the temperature of the adduct was maintained between 25°–30° C. A white precipitate started to appear after nearly one-third of the hydrocyanic acid was added, and turned into oil at the end of the addition of hydrocyanic acid. After the addition of hydrocyanic acid was over, the mixture was stirred for one hour and cooled to 10°–15° C., the oil solidified and the precipitate was filtered, washed with water and dried. Twenty-seven grams of methylene-bis-iminodiacetonitrile, the precipitate, were recovered in 95.5% yield. The compound has a melting point of 83°–85° C. and a C, H, N analysis as compared with the theoretical as follows:

|   | Found | Theoretical |
|---|-------|-------------|
| C | 53.8% | 54.0% |
| H | 5.1%  | 5.0%  |
| N | 41.1% | 41.0% |

EXAMPLE 2

Nitrilotriacetonitrile from Methylene-bis-Iminodiacetonitrile.

Methylene-bis-iminodiacetonitril (20.2g; 0.1 mole) was charged to a reactin flask containing 50 ml of water heated to 60° C. until most of the solid was dissolved. Liquid hydrocyanic acid (5.4 g; 0.2 mole) was added at the rate of 0.44 ml/min.; the addition of formaldehyde (7.5 ml; 0.1 mole) was started, after all the addition of hydrocyanic acid was over. An excess of hydrocyanic acid was added during the addition of formaldehyde. During the additions, the mixture of methylene-bis-iminodiacetonitrile and hydrocyanic acid was always kept at a slight reflux. After the addition of formaldehyde and hydrocyanic acid was over, the solution was refluxed for 2½ hours, the temperature being between 80°–90° C. During this period, the color of the solution changed to light yellow and crystals started to appear. After 2½ hours, the flask was cooled to 10°–15° C., the crystals were filtered, washed with water and dried. Twenty-four grams of nitrilotriacetonitrile, the crystals, were recovered in 90% yield and in 99% purity as determined by alkaline hydrolysis to trisodium nitrilotriacetate.

In the following Examples 3 to 6, nitrilotriacetonitrile is produced by means of the methylene-bis-iminodiacetonitrile intermediate but without isolating the intermediate. In Examples 3 to 5, the initial formaldehyde to ammonia ratios are varied. In Example 6, a three cycle process is used where the filtrate from each cycle serves as solvent for the next cycle.

EXAMPLE 3

In this example, an initial formaldehyde to ammonia molar ratio of 3:2 was used. Formaldehyde (31.5 ml; 0.42 mole) was charged into a reaction flask. Anhydrous ammonia gas (4.76 g; 0.28 mole) was metered to the flask, in such a rate that the temperature of the flask did not go above 25° C. The ammonia-formaldehyde adduct was stirred for one hour. Formaldehyde (21.5 ml; 0.28 mole) was added, the pH was adjusted to 1 by addition of concentrated sulfuric acid. The adduct was warmed to 30°–35° C. and hydrocyanic acid (21.5 ml; 0.56 mole) was added at an appropriate rate. After the addition of hydrocyanic acid was over, the reaction mixture was stirred for one hour, and then the temperature was raised to 55°–60° C.; then further addition of hydrocyanic acid (10.7 ml; 0.28 mole) was started. Addition of formaldehyde (10 ml; 0.14 mole) was started after nearly half of hydrocyanic acid was added. A 10% excess of hydrocyanic acid was added and the reaction product was refluxed for 2½ hours, crystals started to appear during that period. The mixture was cooled to 10°–15° C., filtered and the solid, nitrilotriacetonitrile, was dried. Thirty-five and one half grams were recovered in a 95–96% yield.

EXAMPLE 4

In this example an initial formaldehyde to ammonia molar ratio of 3:1 was used. Formaldehyde (63 ml; 0.84 mole) was charged into a 100 ml. reaction flask and cooled to 10°–15° C. by pumping cold water through the jacket. Then anhydrous amonia gas (4.76 gms; 0.28 mole) was added at such a rate that the temperature did not increase above 25° C. after the addition of ammonia was over. The solution was stirred for twenty minutes and the pH of the solution was adjusted to one by addition of concentrated sulfuric acid. The temperature of the ammonia-formaldehyde adduct was raised to 30° to 35° C. and the addition of liquid hydrogen cyanide was started at the rate of 0.44 ml/min. (21.5 ml). A white solid started to form after nearly half of hydrocyanic acid was added. After the addition of hydrogen cyanide was over, the temperature of the bath was raised to 55°–60° C., and another batch of hydrogen cyanide (10.0 ml) was added at the same rate. and after the addition, the temperature remained at 55°–75° C. and raised to 80°C. at the last half hour of addition. The mixture was refluxed for 2 hours after addition of liquid hydrogen cyanide the crystals of nitrilotriacetonitrile appear. The mixture was then cooled, after refluxing was over, washed and dried. Thirty-six and one half grams of nitrilotriacetonitrile were recovered in a 97–98% yield.

EXAMPLE 5

In this example an initial formaldehyde to ammonia molar ratio of 2.5:1 was used. Formaldehyde (52.5 ml; 0.70 mole) was charged to a reaction flask and cooled to 10°–15° C. Ammonia (0.28 mole) was passed into the solution, in such a rate, the temperature did not increase above 25° C. After all the ammonia was added, the ammonia-formaldehyde adduct was stirred for 30 minutes and the pH of the solution was adjusted to one by the addition of sulfuric acid. The liquid cyanide (21.5 ml; 0.56 mole) was passed into the solution at the rate of 0.44 ml/min. the temperature of the adduct was maintained between 25°–30° C. After the addition was over, the temperature was raised to 55°–60° C., further hydrocyanic acid (15.00 ml) was pumped at the same rate. After nearly half of the hydrocyanic acid was added, formaldehyde (10.5 ml; 0.14 mole) was pumped simultaneously, keeping the solution in the flask under reflux. After the additions were over, the mixture was refluxed (maximum temperature 85° C.) for 2 hours. During this process, fine crystals of nitrilotriacetonitrile appear. The mixture was cooled, filtered and the crystals were dried. Thirty-six and one half grams of nitrilotriacetonitrile were recovered in a 97–98% yield.

EXAMPLE 6

(Cycle 1). Formaldehyde (31.5 ml; 0.42 mole) was charged into a reaction flask and cooled to 10°–15° C. Ammonia (0.28 mole) was passed into the solution at such a rate that the temperature did not increase above 25° C. After the addition was over, the ammonia-formaldehyde adduct was stirred for one hour, another batch of formaldehyde (21.0 ml; 0.28 mole) was added, pH was adjusted to one, and hydrogen cyanide (21.5 ml; 0.57 mole) was added at the rate of 0.44 ml/min. The temperature at the time of addition was maintained between 25°–30° C. After the addition was over, the temperature was raised to 55°–60° C., further hydrogen cyanide (10.75 ml; 0.14 mole) was pumped simultaneously, and keeping the solution in the flask under reflux. After the addition was over, the mixture was refluxed for 2 hours. Crystals of nitrilotriacetonitrile started to appear during this period. Then the mixture was cooled, filtered and the crystals were dried. Thirty-five and one half grams of nitrilotriacetonitrile were recovered in 95-95% yield.

(Cycle 2). Filtrate of the above reaction was taken in the reaction flask and formaldehyde was charged into a reaction flask in the same manner and number of moles as above. The experiment was repeated as described above. Fine crystals, as observed in the first paragraph, did not appear in the last stage although a precipitate (solid) did appear. A light brown product of nitrilotriacetonitrile was obtained in an amount of 35.5 grams in 95–96% yield.

(Cycle 3). Filtrate of reaction (2) was taken in the reaction flask and the reaction as described in reaction (1) was repeated. No crystals appeared at the final stage of the reaction but a solid (nitriloacetonitrile) did precipitate on cooling in an amount of 32 grams and 86% yield.

EXAMPLE 7

Nitrilotriacetic Acid from Methylene-Bis-Iminodiacetonitrile.

Sodium hydroxide (8.4 g or 0.210 mole) was dissolved in 12 ml of water and the solution was placed in a 100 ml reaction flask equipped with a stirrer, reflux condenser and an addition funnel. Sodium cyanide (2.46 g or 0.0502 mole) as a 30% solution was added and the solution heated to reflux temperature. A hot solution of 5 g of (0.0247 mole) methylene-bis-iminodiacetonitrile in 30 ml of hot water was added and ammonia started to evolve. After 15 minutes an additional 2.46 g of sodium cyanide was added and 5 g of methylene-bis-iminodiacetonitrile was added slowly over a period of 30 minutes. After the addition of methylene-bis-iminodiacetonitrile was completed, 3.8 ml of a 40% aqueous formaldehyde solution (0.0506 moles) was added over a period of 1 hour. The resulting reddish yellow solution was heated until all ammonia was removed. After cooling the solution was decolorized with charcoal and diluted to a specific gravity of 1.324 at 25° C. Calcium titration showed the yield of nitrilotriacetic acid to be 71% of theory.

EXAMPLE 8

In this example, all the hydrogen cyanide and formaldehyde were added in the first step and nitrilotriacetonitrile was prepared without isolation of the methylenebis-iminodiacetonitrile intermediate.

A 200 ml. jacketed reaction flask was charged with formaldehyde solution (0.9 mole; 73 ml. of 37% HCHO) and cooled to 15°–20° C. Ammonia (0.3 mole; 5.1 g) was added to formaldehyde solution in such a rate the temperature did not increase above 30° C. Then 5 ml. of concentrated sulfuric acid was added to decrease the pH to 1 and the temperature of the adduct was adjusted to 30° C. Liquid hydrogen cyanide (0.9 mole; 24.3 g) was added at the rate of 0.3 g/min. to the adduct and the temperature of the adduct was not allowed to rise above 35° C. After the addition of hydrogen cyanide was over, the temperature was raised to 65°–70° C. and kept at that temperature range for 30 minutes and the mixture was refluxed for 15–30 minutes. A white crystalline solid, nitrilotriacetonitrile, appeared which was filtered off and dried. Yield: 38.5 g.; 95% of the theoretical based on formaldehyde.

Examples 9 through 15 illustrate the addition of ammonia and hydrogen cyanide to the fully formed ammonia-formaldehyde adduct.

EXAMPLE 9

In this example, ammonia and hydrogen cyanide are added to the fully formed ammonia-formaldehyde adduct.

A 100 ml. jacketed reaction flask was charged with formaldehyde (0.9 ml; 70 ml. containing a total of 27 g. of HCHO) and ammonia (0.3 m.; 5.1 g) was added as usual in such a way that the temperature did not rise above 30° C. The formaldehyde to ammonia molar ratio was 3:1. Then the pH of the adduct was lowered to one by the addition of concentrated sulfuric acid. Then ammonia (0.2 m.; 3.48 g.; 0.042 g./min.) and hydrogen cyanide (0.9 m.; 35.5 ml.; 0.44 ml./min.) were simultaneously added for 80 minutes. The ammonia and hydrogen cyanide were added in a molar ratio of 1:4.5. The addition temperature was maintained between 60°–65° C. After the addition was over, it was refluxed for 2 hours. The yield was 23 grams of nitrilotriacetonitrile, which represented a conversion based on ammonia of 34.3%, on formaldehyde of 57.4% and on hydrogen cyanide of 57.4%.

EXAMPLE 10

In this example, ammonia and hydrogen cyanide are added in two steps (different step temperatures) to the fully formed ammonia - formaldehyde adduct.

A 100 ml. jacketed reaction flask was charged with formaldehyde (0.9 m.; 27 g.; 70 ml.) and ammonia (0.3 m.; 5.1 g.) was added as usual in such a way the temperature did not raise above 30° C. The formaldehyde to ammonia molar ratio was 3:1. Then the pH of the adduct was lowered to one (1) by the addition of the concentrated sulfuric acid. Then ammonia (0.042 g./min.) and liquid hydrogen cyanide (0.44 ml./min.) were added for 54 minutes, the temperature being maintained between 30°–35° C. The ammonia and hydrogen cyanide were added in a molar ratio of 1:4.5. A white preciptiate appeared at the end of the addition. Then the temperature was raised to 60°–65° C., and ammonia and hydrogen cyanide were added at the same rate for 27 minutes. After the addition was over, it was refluxed for 30 minutes, cooled, filtered and the product dried. The yield was 34 grams of which 34% was nitrilotriacetonitrile, 23% iminodiacetonitrile and 53% methylene-bis-iminodiacetonitrile. This represented a conversion to products based on ammonia of 49.4%, on formaldehyde of 87.3% and on hydrogen cyanide of 79.4%.

EXAMPLE 11

In this example, ammonia and hydrogen cyanide are added to the fully formed ammonia - formaldehyde adduct at a constant temperature (30°–35° C.).

A 100 ml. jacketed reaction flask was charged with formaldehyde solution (0.75 m.; 22.5 g.; 58.3 ml.) and enough ammonia to establish a 2.5:1 molar ratio of $HCHO:NH_3$. The pH of the solution was lowered to one (1) by the addition of concentrated sulfuric acid. Then ammonia (0.2 m.; 3.4 g.) and hydrogen cyanide (0.6 m.; 16.2 g.; 23.7 ml.) were added for 54 minutes, maintaining the temperature between 30°–35° C. The ammonia and hydrogen cyanide were added in a molar ratio of 1:4.5. After the addition was over it was cooled and filtered and dried. The yield was 30 grams of methylene-bis-iminodiacetonitrile, which represented a conversion based on ammonia of 59.4%, on formaldehyde of 99% and on hydrogen cyanide of 99%.

EXAMPLE 12

In this example, ammonia and hydrogen cyanide were added to the fully formed ammonia - formaldehyde adduct, and then only hydrogen cyanide was added.

A 100 ml. jacketed flask was charged with formaldehyde (0.9 m.; 27 g.; 70 ml.) and ammonia (0.3 m.; 5.1 g.) was added as usual in such a way the temperature did not raise above 30° C. The formaldehyde to ammonia molar ratio was 3:1. Then the pH of the adduct was lowered to 1 by the addition of concentrated sulfuric acid. Then ammonia (0.042 g./min.) and liquid hydrogen cyanide (0.44 ml./min.) were added for 54 minutes, the temperature being maintained between 30°–35° C. The ammonia and hydrogen cyanide were added in a molar ratio of 1:4.5. A white precipitate appeared at the end of the addition. Then the temperature was raised to 65°–70° C., then only hydrogen cyanide was added at the rate of 0.44 ml./min. for 27 minutes. After the addition was over, it was refluxed for 30 minutes, cooled, and filtered and the product dried. The yield was 31 grams of which 68% was nitrilotriacetonitrile and 29.4% methylene-bis-iminodiacetonitrile. This represented a conversion to products based on ammonia of 49.4%, on formaldehyde of 87.3% and on hydrogen cyanide of 79.4%.

EXAMPLE 13

In this example, ammonia and hydrogen cyanide (molar ratio of 1:4.5 in the first stage and 1:9 in the second stage) were added to the fully formed ammonia - formaldehyde adduct.

A 100 ml. jacketed reaction flask was charged with formaldehyde (0.9 m.; 27 g.; 70 ml.) and ammonia (0.3 m.; 5.1 g) was added as usual in such a way that the temperature did not raise above 30° C. The formaldehyde to ammonia molar ratio was 3:1. Then the pH of the adduct was lowered to 1 by the addition of concentrated sulfuric acid. Then ammonia (0.042 g./min.) and liquid hydrogen cyanide (0.44 ml./min.) were added for 54 minutes, the temperature being maintained between 30°–35° C. The ammonia and hydrogen cyanide were added in a molar ratio of 1:4.5. A white solid appeared at the end of the addition. Then the temperature was raised to 60°–65° C., ammonia and hydrogen cyanide were added in the ratio of 1:9 at the rates of 0.021 g/min. and 0.44 ml./min. respectively for 27 minutes. After the addition was over it was refluxed for 30 minutes, cooled and filtered and the product dried. The yield of nitrilotriacetonitrile was 36 grams. This represented a conversion based on ammonia of 57.5% on formaldehyde of 90.0% and on hydrogen cyanide of 90.0%.

The above experiment was repeated and the yield was 36 grams of which 94.5% was nitrilotriacetonitrile and 2.9% was methylene-bis-iminodiacetonitrile.

EXAMPLE 14

In this example, ammonia and hydrogen cyanide (molar ratio of 1:4.5 in the first stage and 1:18 in the second stage) are added to the fully formed ammonia formaldehyde adduct.

A 100 ml. jacketed flask was charged with formaldehyde (0.9 m.; 27 g.; 70 ml.) and ammonia (0.3 m.; 5.1 g.) was added as usual in such a way the temperature did not raise above 30° C. Then the pH of the adduct was lowered to 1 by the addition of concentrated sulfuric acid. Then ammonia (0.042 g./min.) and liquid hydrogen cyanide (0.44 ml./min.) were added for 54 minutes, the temperature being maintained between 30°–35° C. The ammonia and hydrogen cyanide were added in a molar ratio of 1:4.5. A white precipitate appeared at the end of the addition. Then the temperature was raised to 60°–65° C., ammonia and hydrogen cyanide were added at the rates of 0.0105 g./min. and 0.44 ml./min. respectively for 27 minutes. The ammonia and hydrogen cyanide were added in a molar ratio of 1:18. After the addition was over, it was refluxed for 30 minutes, cooled and filtered and the product dried. The yield was 39 grams of nitrilotriacetonitrile which represented a conversion based on ammoni of 64.6%, on formaldehyde of 97% and on hydrogen cyanide of 97%.

EXAMPLE 15

In this example, ammonia and hydrogen cyanide (molar ratio of 1:4.5 in the first stage and 1:6 in the second stage) are added to the fully formed ammonia - formaldehyde adduct.

A 100 ml. jacketed reaction flask was charged with formaldehyde (0.9 m.; 27 g.: 70 ml.) and ammonia (0.3 m.; 5.1 g.) was added as usual in such a way the temperature did not raise above 30° C. Then the pH of the adduct was lowered to 1 by the addition of concentrated sulfuric acid. Then ammonia (0.042 g./min.) and liquid hydrogen cyanide (0.44 ml./min.) were added for 54 minutes, the temperature being maintained between 30°–35° C. The ammonia and hydrogen were added in a molar ratio of 1:4.5. A white solid appeared at the end of the addition. Then the temperature was raised to 60°–65° C., ammonia and hydrogen cyanide were added at the rates of 0.0315 g./min. and 0.0440 ml./min. respectively for 27 minutes. The ammonia and hydrogen cyanide were added in a molar ratio of 1:6. After the addition was over, it was refluxed for 30 minutes, cooled and filtered and the product dried. The yield was 34 grams of which 91% was nitrilotriacetonitrile and 4.4% was methylene-bis-iminodiacetonitrile. This represented a conversion to products based on ammonia of 56.4%, on hydrogen cyanide of 79.9% and on formaldehyde of 80.3%.

Examples 16 through 22 illustrate the addition of ammonia and hydrogen cyanide to the partially formed ammonia-formaldehyde adduct.

EXAMPLE 16

In this example, ammonia and hydrogen cyanide (molar ratio of 1:4.5) are added to the partially formed ammonia-formaldehyde adduct at a constant temperature (30°–35° C.)

Formaldehyde solution (0.9 m.; 27 g.; 68.5 ml.) was charged into a 100 ml. jacketed flask cooled to 20° C. Ammonia (0.1 m.; 17 g.) was added at the rate of 0.072 g./min. for 24 minutes. The formaldehyde to ammonia molar ratio was 9:1. Then the pH was adjusted to one by the addition of concentrated sulfuric acid. Then, ammonia (0.2 m.; 3.4 g.) and hydrogen cyanide (0.9 m.; 23.6 g.) were added simultaneously at the rate of 0.072 g./min. and 0.75 ml./min. for 47 minutes. The ammonia and hydrogen cyanide were added in a molar ratio of 1:4.5. The temperature was maintained between 30°–35° C. during the addition. A white solid was observed at the end of the addition. It was heated to 60°–65° C. for 90 minutes, cooled; an oil had formed. After seeding the oil, a solid crystallized out. The yield was 19 grams of methylene-bis-iminodiacetonitrile, which represented a conversion based on ammonia of 62.7%, on formaldehyde of 52.2% and on hydrogen cyanide of 41.8%.

EXAMPLE 17

In this example, ammonia and hydrogen cyanide (molar ratio of 1:4.5) are added to the partially formed ammonia - formaldehyde adduct at a constant temperature (60°–65° C.).

Formaldehyde solution (0.9 m.; 27 g.; 68.5 ml.) was charged into a 100 ml. jacketed reaction flask cooled to 20° C. Ammonia (0.1 m.; 1.7 g.) was added at the rate of 0.072 g./min. for 24 minutes. The formaldehyde to ammonia molar ratio was 9:1. Then the pH was adjusted to one by the addition of concentrated sulfuric acid. Then, ammonia (0.2 m.; 3.4 g.) and hydrogen cyanide (0.9 m.; 23.6 g.) was added simultaneously at the rate of 0.072 g./min. and 0.75 ml./min. for 47 minutes maintaining the temperature at 60°–65° C. The ammonium and hydrogen cyanide were added in a molar ratio of 1:4.5. After refluxing for 30 minutes, it was cooled, filtered, and the solid collected, dried and weighed. The yield was 19 grams of nitrilotriacetonitrile, which represented a conversion based on ammonia of 47%, on hydrogen cyanide of 47% and on formaldehyde of 47%.

EXAMPLE 18

In this example, ammonia and hydrogen cyanide (a molar ratio of 1:4.5) are added to the partially formed ammonia - formaldehyde adduct in two stages (temperature of the first stage was 30°–35° C., and the second was 60°–65° C.).

Formaldehyde (0.9 m.; 27 g.; 70 ml.) was charged to 200 ml. jacketed flask and ammonia (0.1 m.; 1.7 g.) was added for 8.50 minutes at the rate of 0.6 cft./hr. The formaldehyde to ammonia molar ratio was 9:1. Then the pH of the adduct was lowered to one by the addition of concentrated sulfuric acid. Then the temperature was adjusted to 30° C., ammonia and hydrogen cyanide were added simultaneously at the rate of 0.042 g./min. and 0.44 ml/min. respectively for 54 minutes. The ammonia and hydrogen cyanide were added in a molar ratio of 1:4.5. No solid was observed during the addition. After the addition was over, the temperature was raised to 65° C., ammonia and hydrogen cyanide were added for 27 minutes at the same rate. After addition, it was refluxed up to 85°–90° C. for 40 minutes. As usual it was cooled, filtered, and a solid was obtained and dried. The yield was 30 grams of nitrilotriacetonitrile, which represented a conversion based on ammonia of 80%, on hydrogen cyanide of 80% and on formaldehyde of 80%.

EXAMPLE 19

In this example, ammonia and hydrogen cyanide are added to the partially formed ammonia - formaldehyde adduct in two stages (molar ratio of $NH_3$:HCN in the first stage was 1:9). Also, more formaldehyde was added in the second stage.

A 200 ml. jacketed reaction flask was charged with formaldehyde solution (0.75 m.; 22.5 g.; 57.5 ml.) and then ammonia (0.2 m.; 3.4 g.) was added at the rate of 0.48 g. per minute for 7.08 minutes. Then the pH of the solution was adjusted to one by the addition of concentrated sulfuric acid. Then ammonia and hydrogen cyanide were added simultaneously at the rate of 0.021 g./min. and 0.44 ml./min respectively for 54 minutes. The ammonium and hydrogen cyanide were added in a molar ratio of 1:9. After that addition, the temperature was raised to 65°–70° C., ammonia and hydrogen cyanide addition were continued along with formaldehyde (0.15 m.; 11.5 ml.), for 27 minutes. After the addition, it was refluxed for 30 minutes and then cooled, filtered, and the solid obtained was dried and weighed. The yield was 35.5 grams of nitrilotriacetonitrile, which represented a conversion based on ammonia of 88.3%, on hydrogen cyanide of 88.4% and on formaldehyde of 88.4%.

EXAMPLE 20

In this example, ammonia and hydrogen cyanide are added to the partially formed ammonia - formaldehyde adduct in two stages (molar ratio of $NH_3$:HCN in both stages was 1:7.05). Also, more formaldehyde is added in the second stage.

Formaldehyde solution (0.75m.;22.5ml.;57.5ml.) was charged into a 200 ml. jacketed reaction flask and cooled to 20° C. Ammonia (0.1724m.; 2.9308 g.) was passed at the rate of 0.48g./min. for 6.1 min. Then the pH of the solution (adduct) was reduced to 1 by the addition of concentrated sulfuric acid. The temperature was raised to 30° and ammonia and hydrogen cyanide were passed simultaneously at the rate of 0.0267g./min. and 0.44ml./min. respectively for 54 minutes. The ammonia and hydrogen cyanide were added in a molar ratio of 1:7.05. A white solid was formed during the end of the addition. Then the pH was adjusted to 1 if it had been changed above 1 by the addition of concentrated sulfuric acid. Then the temperature was raised to 65°–70° C, and then the addition of ammonia and hydrogen cyanide at the same rates was continued along with formaldehyde solution (0.15m.; 4.5 g.; 11.5 ml.) for 27 minutes. As observed in other cases, a white solid in yellow solution started to crystallize out. After the addition, it was refluxed for 30 minutes; cooled to 20°, filtered, and the solid obtained was dried and weighed. The yield was 32 grams of nitrilotriacetonitrile, which represented a conversion based on ammonia of 75.8%, on hydrogen cyanide of 79.6% and on formaldehyde of 79.6%.

The experiment was repeated and the yield was 36 grams of nitrilotriacetonitrile, which represented a conversion based on ammonia of 85.8%, on hydrogen cyanide of 89.6%, and on formaldehyde of 89.6%.

EXAMPLE 21

In this example, ammonia and hydrogen cyanide (molar ratio of 1:4.5) are added to the partially formed ammonia-formaldehyde adduct in two stages (each stage being at a different temperature). Also, more formaldehyde is added in the second stage.

A 200 ml. jacketed reaction flask was charged with formaldehyde solution (0.75 m.; 2.55 g.; 60.08 ml.) and ammonia was added (0.167 m.; 2.839 g.) at the rate of 0.48 g./min. for 5.91 minutes keeping the temperature below 30° C. Then ammonia and hydrogen cyanide were added simultaneously after the addition of concentrated sulfuric acid at the rate of 0.042 g./min. and 0.44 ml./min. respectively for 54 minutes. Then the temperature was raised to 65°–70° C. and kept there for 27 minutes; the addition of ammonia and hydrogen cyanide at the same rates was continued along with formaldehyde solution (0.15 m.; 4.5 g.; 11.5 ml.). Then it was refluxed for 30 minutes, cooled to 20°; the crystals formed were collected over the Buchner funnel, and dried. The yield was 36.0 grams of nitrilotriacetonitrile which represented a conversion based on ammonia of 90%, on hydrogen cyanide of 90%, and on formaldehyde of 90%.

EXAMPLE 22

In this example, which appears to produce the best results, ammonia and hydrogen cyanide (molar ratio of 1:4.5) are added to partially formed ammonia-formaldehyde adduct (molar ratio of 4.25:1) in the first stage (at 30°–35° C.). Then, in the second stage (at 60°–65° C.), hydrogen cyanide, plus formaldehyde, is added.

A 200 ml. jacketed reaction flask was charged with formaldehyde solution (0.75 m.; 22.5 g.; 60.08 ml.) and ammonia was added (0.2113 m.; 3.5921 g.) at the rate of 0.48 g./min., for 7.48 minutes, keeping the temperature below 30°–35° C. The ammonia to formaldehyde molar ratio was 4.25:1. Then ammonia and hydrogen cyanide were added simultaneously, after the addition of concentrated sulfuric acid (to lower the pH to one), at the rate of 0.042 g./min. and 0.44 ml./min. for 54 minutes. The ammonia and hydrogen cyanide were added in a molar ratio of 1:4.5. Then the temperature was raised to 65°–70° C., the addition of liquid hydrogen cyanide was continued at the same rate, along with formaldehyde solution (0.15 m.; 4.5 g.; 11.5 ml.), for 27 minutes. Then it was refluxed for 30 minutes, cooled to 20° C.; the crystals obtained were collected on a Buchner funnel and dried. The yield was 38.5 grams of nitrilotriacetonitrile, which represented a conversion based on ammonia of 95.5%, on hydrogen cyanide of 95.5%, and on formaldehyde of 95.5%.

I claim:
1. The method of preparing methylene-bis-iminodiacetonitrile which comprises forming a liquid phase adduct of ammonia and formaldehyde, adjusting the pH of said liquid phase below about 2 and adding hydrogen cyanide to said liquid phase maintained at a pH below about 2 and a temperature below about 50° C. to form methylene-bis-iminodiacetonitrile.
2. The method of claim 1 in which the pH is maintained at a value not more than about 1.
3. The method of claim 1 in which the temperature is maintained between about 10° and about 35° C.
4. The method of claim 1 in which the pH is maintained at a value not more than about 1 and the temperature between about 10° and about 35° C.
5. The method of preparing nitrilotriacetonitrile which comprises reacting methylene-bis-iminodiacetonitrile in the liquid phase at a temperature below about 95° C. with hydrogen cyanide and formaldehyde to form nitrilotriacetonitrile.
6. The method of claim 5 in which formaldehyde is added to a liquid phase mixture of methylene-bis-iminodiacetonitrile and hydrogen cyanide.
7. The method of claim 5 in which hydrogen cyanide is added to a liquid phase mixture of methylene-bis-iminodiacetonitrile and formaldehyde.

8. The method of claim 5 in which the temperature is maintained between about 50° and about 85° C.

9. The method of preparing nitrilotriacetonitrile which comprises forming a liquid phase adduct of ammonia and formaldehyde, maintaining the pH of said liquid phase below about 2, adding hydrogen cyanide to said liquid phase to form methylene-bis-iminodiacetonitrile and reacting the methylene-bis-iminodiacetonitrile with hydrogen cyanide and formaldehyde to form nitrilotriacetonitrile.

10. The method of claim 9 in which all the formaldehyde is added in the step in which the adduct of ammonia and formaldehyde is formed.

11. The method of claim 9 wherein the nitrilotriacetonitrile is separated from the reaction mixture and the portion of the reaction mixture separated from the nitrilotriacetonitrile is returned to the step of formation of methylene-bis-iminodiacetonitrile.

12. The method of claim 9 in which hydrogen cyanide is added to the liquid phase containing the methylene-bis-iminodiacetonitrile and then formaldehyde is added.

13. The method of claim 9 in which formaldehyde is added to the liquid phase containing the methylene-bis-iminodiacetonitrile and then liquid hydrogen cyanide is added.

14. The method of claim 9 in which all the hydrogen cyanide is added in the step in which the adduct of ammonia and formaldehyde which has been adjusted to a pH below about 2 is reacted to form methylene-bis-iminodiacetonitrile.

15. The method of preparing nitrilotriacetonitrile which comprises forming a liquid phase adduct of ammonia and formaldehyde, adjusting the pH of said liquid phase below about 2, adding ammonia and hydrogen cyanide to said liquid phase maintained at a temperature below about 50° C. and a pH below about 2 to form methylene-bis-iminodiacetonitrile and reacting the methylene-bis-iminodiacetonitrile at a temperature below about 95° C. with hydrogen cyanide and formaldehyde to form nitrilotriacetonitrile.

16. The method of claim 15 wherein the ammonia and hydrogen cyanide are added in two stages, each stage at a different temperature.

17. The method of claim 16 wherein a portion of the stoichiometrically necessary formaldehyde is not added until the second stage.

18. The method of claim 15 wherein the ammonia and hydrogen cyanide are added in a first stage at one temperture, and hydrogen cyanide by itself is added in a second stage at another temperature.

19. The method of claim 15 wherein the molar ratio of the ammonia to the formaldehyde in the adduct lies between about 1:2.5 to about 1:9.

20. The method of preparing methylene-bis-iminodiacetonitrile of claim 1 which comprises forming an aqueous liquid phase adduct of ammonia and formaldehyde, adjusting the pH of said liquid phase between about 0 and about 2 by the addition of a strong mineral acid, adding hydrogen cyanide to said liquid phase maintained at a pH between about 0 and 2 and a temperature between about 10° and 50° C. to form methylene-bis-iminodiacetonitrile.

21. The method of claim 20 wherein the strong mineral acid is selected from the group consisting of sulfuric and hydrochloric acid.

22. The method of preparing methylene-bis-iminodiacetonitrile of claim 20 wherein the ratio of ammonia and formaldehyde utilized in the process is between about 1:1.5 and 1:3 and the ratio of ammonia and hydrogen cyanide is between about 1:1.2 and 1:3.

23. The method of preparing nitrilotriacetonitrile of claim 5 which comprises reacting methylene-bis-iminodiacetonitrile with hydrogen cyanide and formaldehyde in an aqueous liquid phase mixture at a temperature between about 50° C. and about 95° C. to form nitrilotriacetonitrile.

24. The method of preparing nitrilotriacetonitrile of claim 23 which comprises reacting methylene-bis-iminodiacetonitrile at a pH between about 0 and about 2 with hydrogen cyanide and formaldehyde to form nitrilotriacetonitrile.

25. The method of preparing nitrilotriacetonitrile of claim 24 wherein the pH is maintained between about 0 and about 2 by the presence of a strong mineral acid selected from the group consisting of sulfuric and hydrochloric acid.

26. The method of preparing nitrilotriacetonitrile which comprises: forming an aqueous liquid phase adduct of ammonia and formaldehyde, adjusting the pH of said liquid phase below about 2, adding hydrogen cyanide to said liquid phase maintained at a pH below about 2 and a temperature below about 50° C. to form a reaction mixture containing methylene-bis-iminodiacetonitrile and reacting the methylene-bis-iminodiacetonitrile in the reaction mixture with hydrogen cyanide and formaldehyde at a temperature between 50° C. and about 95° c. to form nitrilotriacetonitrile.

27. The method of preparing nitrilotriacetonitrile of claim 26 which comprises; forming a liquid phase adduct of ammonia and formaldehyde, adjusting the pH of said liquid phase between about 0 and 2 by the addition of a mineral acid, adding hydrogen cyanide to said liquid phase maintained at a pH between about 0 and about 2 by the presence of a mineral acid and a temperature between about 10° and 50° C. to form a reaction mixture containing methylene-bis-iminodiacetonitrile and reacting said methylene-bis-iminodiacetonitrile in said reaction mixture with hydrogen cyanide and formaldehyde at a temperature between 50° and about 95° C. and a pH between about 0 and about 2 to form nitrilotriacetonitrile.

28. The method of preparing nitrilotriacetonitrile of claim 27 wherein said ammonia, formaldehyde and hydrogen cyanide are utilized in a ratio of ammonia:-formaldehye of from about 1:1.8 to about 1.3.6 and a ratio of ammonia:hydrogen cyanide of from about 1:1.8 to about 1:3.6.

29. The method of preparing nitrilotriacetonitrile of claim 15 which comprises forming a liquid phase adduct of ammonia and formaldehyde, adjusting the pH of said liquid phase between about 0 and about 2 by addition of a strong mineral acid adding ammonia and hydrogen cyanide to said liqued phase maintained at a pH between about 0 and about 2 by the presence of a strong mineral acid and at a temperature between about 10° and 50° C. to form a reaction mixture containing methylene-bis-iminodiacetonitrile and adding hydrogen cyanide and ammonia to said reaction mixture maintained at a temperature between 50° and about 95° C. and a pH between about 0 and 2 to form nitrilotriacetonitrile, said ammonia, formaldehyde and hydrogen cyanide are added to the reaction mixture in a ratio of ammonia:formaldehyde of from about 1:1.8 to about 1:3.6 and of ammonia:hydrogen cyanide of from about 1:1.8 to about 1:3.6.

30. The method of preparing methylene-bis-iminodiacetonitrile which comprises forming an aqueous liquid phase adduct of ammonia and formaldehyde, adjusting the pH of said liquid phase between about 0 and about 2 by the addition of a strong mineral acid, adding ammonia and hydrogen cyanide to said liquid phase maintained at a pH between about 0 and about 2 by the presence of a strong mineral acid and temperature between about 10° and about 50° C. to form methylene-bis-iminodiacetonitrile; said ammonia, formaldehyde and hydrogen cyanide are provided in a formaldehyde:ammonia ratio of from about 1.5:1 to about 3:1 and a hydrogen cyanide:ammonia ratio of from about 1.2:1 to about 3:1.

31. A process for preparing methylenebisiminodiacetonitrile comprising:
 a. reacting at a temperature below about 50° C. for about 16 minutes to 109 minutes a reaction mixture consisting essentially of; (i) water, (ii) an ammonia source selected from the group consisting of an adduct of ammonia and formaldehyde, the adduct of ammonia and formaldehyde being both an ammonia source and a formaldehyde source; (iii) formaldehyde; (iv) HCN; and (v) a strong mineral acid to maintain the pH of the reaction mixture within the range of about 2 –0, the ammonia source, formaldehyde, and HCN being present in amounts to provide a mole ratio of ammonia:formaldehyde:HCN 1:2.5–3:2–3, and the water being present in a ratio of about 10 to 30 parts by weight of water per part by weight of ammonia, to form a reacted mixture consisting essentially of methylenebisiminodiacetonitrile and an acidic liquor;
 b. adjusting the temperature of the reacted mixture to about 10–50° C. if it is not already within this range to form a slurry consisting essentially of crude precipitated crystalline methylenebisiminodiacetonitrile and an acidic mother liquor;
 c. seprating the crude crystalline methylenebisiminodiacetonitrile from the mother liquor while maintaining the temperature of the slurry within the range of about 10° to 50° C.; and
 d. recovering the separated methylenebisiminodiacetonitrile.

32. A fully continuous process for preparing methylenebisiminodiacetonitrile comprising:
 a. charging into a cooled agitated mixing zone, and mixing therein to form an aqueous reaction mixture, reactants consisting essentially of; (i) an ammonia source selected from the group consisting of an adduct of ammonia and formaldehyde, the adduct of ammonia and formaldehyde being both an ammonia source and a formaldehyde source; (ii) an aqueous formaldehyde solution; (iii) a strong mineral acid; and (iv) liquid anhydrous HCN while maintaining the temperature of the reactants in the mixing zone within the rnage of below about 50° C., the mole ratio of ammonia:formaldehyde:HCN in the aqueous reaction mixture being about 1:2.5–3:2–3, the weight ratio of ammonia to water in the aqueous reaction mixture being about 1:10–30; and the pH of the aqueous reaction mixture being about 2–0;
 b. passing the aqueous reaction mixture through a heated reaction zone, residence time in the reaction zone being about 16–109 minutes, while maintaining the temperature of the aqueous mixture in the reaction zone within the range of below about 50° C. to form a reacted mixture consisting essentially of methylenebisiminodiacetonitrile and an acidic aqueous liquor;
 c. adjusting the temperature of the reacted mixture to about 10°–50° C. if it is not already within this temperature range to form crude precipitated crystalline methylenebisiminodiacetonitrile and an acidic mother liquor;
 d. passing the crude precipitated crystalline methylenebisiminodiacetonitrile and the mother liquor through a separating zone to separate the crude crystalline methylenebisiminodiacetonitrile from the mother liquor; and
 e. recovering the separated methylenebisiminodiacetonitrile.

* * * * *